(12) United States Patent
Wang-Lee

(10) Patent No.: US 6,357,053 B1
(45) Date of Patent: Mar. 19, 2002

(54) SAFETY GOGGLES

(76) Inventor: Tzu-Feng Wang-Lee, No. 40, Lane 30, Lung Chung St., Yung Kang Tainan County (TW)

( * ) Notice: Subject to any disclaimer, the term of this patent is extended or adjusted under 35 U.S.C. 154(b) by 0 days.

(21) Appl. No.: 09/727,398

(22) Filed: Nov. 29, 2000

(51) Int. Cl.[7] .................................................. A61F 9/02
(52) U.S. Cl. ............................................. 2/431; 2/453
(58) Field of Search ........................... 2/431, 432, 434, 2/441, 453, 13, 442, 443; 351/47

(56) References Cited

U.S. PATENT DOCUMENTS

| | | | | |
|---|---|---|---|---|
| 3,782,810 A | * | 1/1974 | Marker ......................... | 351/47 |
| 4,901,374 A | * | 2/1990 | Van der Woude .............. | 2/453 |
| 5,379,464 A | * | 1/1995 | Schleger et al. ................ | 2/431 |
| 5,729,321 A | * | 3/1998 | Wielhouwer .................. | 351/44 |
| 6,178,561 B1 | * | 1/2001 | Cheng ........................... | 2/431 |

* cited by examiner

Primary Examiner—John J. Calvert
Assistant Examiner—Katherine Moran
(74) Attorney, Agent, or Firm—Alan Kamrath; Rider, Bennett, Egan & Arundel, LLP

(57) ABSTRACT

A safety goggles comprises a frame including an attachment member projected above the top center and a slanted coupling surface on the top of the attachment member; a lens fitted in the frame; a protector guide; a shade including a frame, an opening defined by the frame, a flange extended inward from the frame, studs on the frame of the shade, projections on either inner side of the flange of the shade, an engagement member projected above the top center of the flange of the shade, and an inclined coupling surface on the top of the engagement member; a protector lens including holes on the periphery being snugly engaged with the studs when the protector lens is fitted into the shade; a dark lens abutted on the protector lens; and an abutment member including alternate risers on the front peripheral edge, the abutment member being abutted on the dark lens within the shade such that the projections is capable of securing the abutment member to the dark lens. The shade is pivotable at an angle of either 90 or 180 degrees with respect to the frame when the inclined coupling surface is slidingly engaged with the slanted coupling surface.

1 Claim, 6 Drawing Sheets

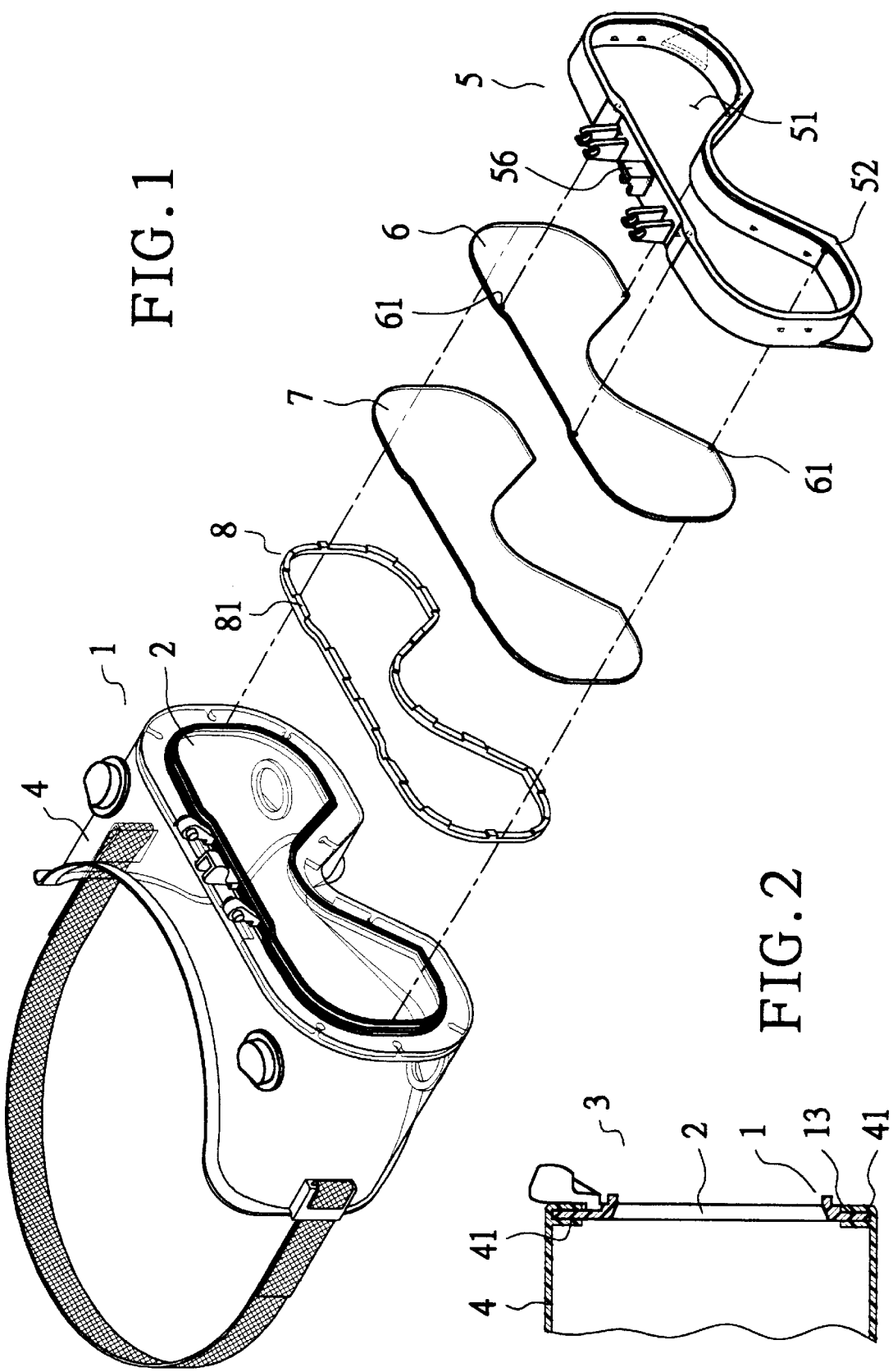

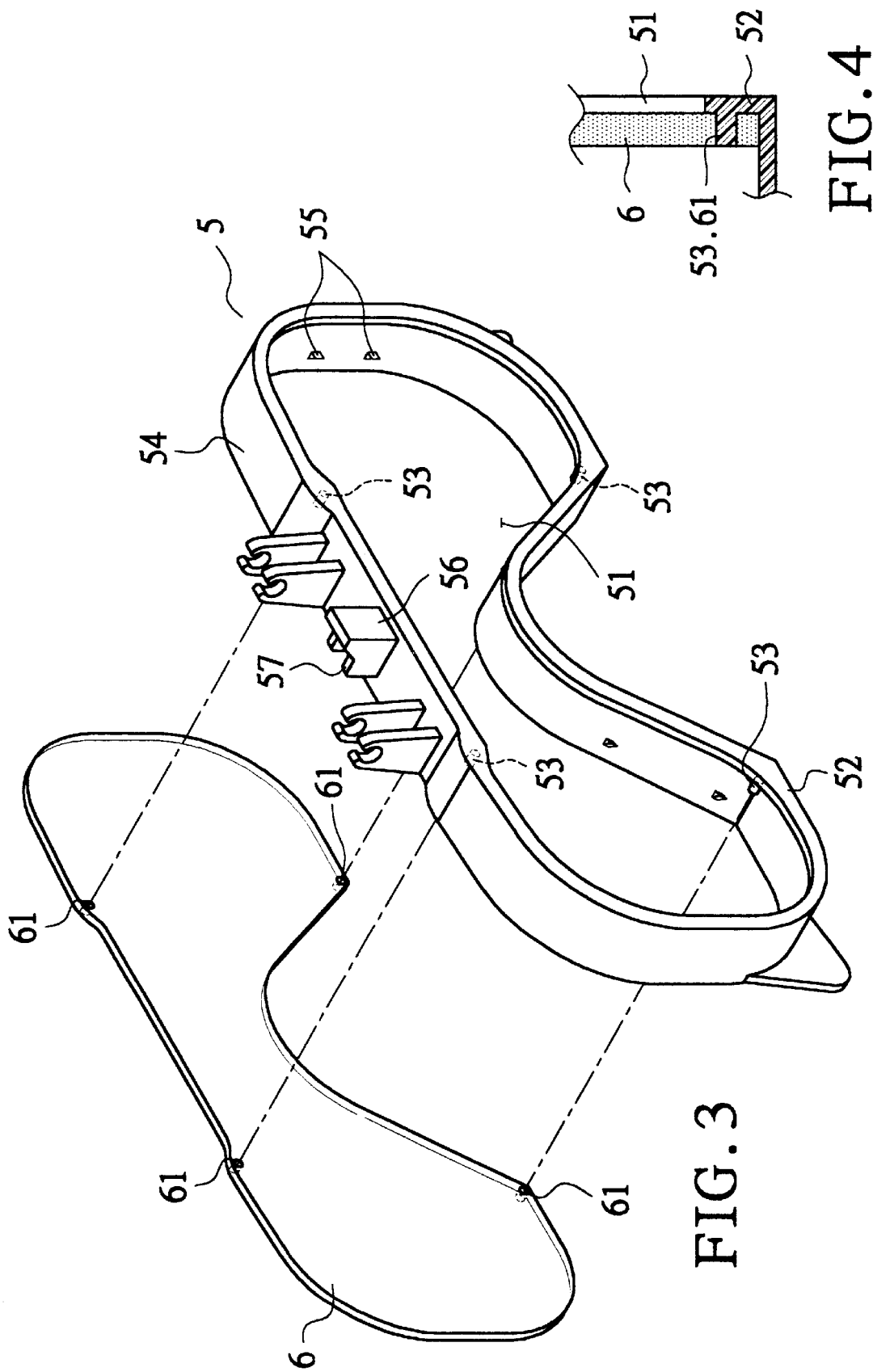

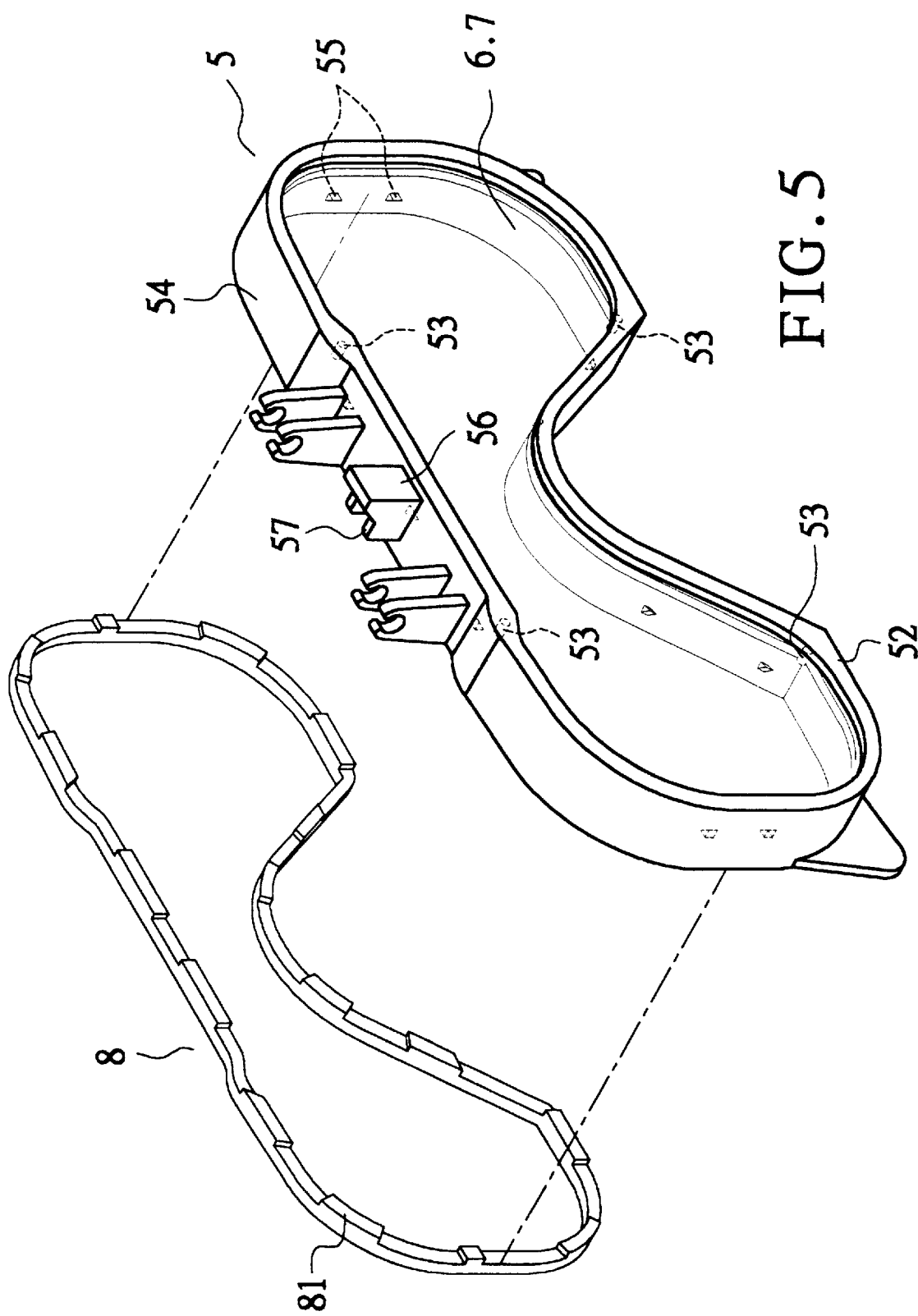

SAFETY GOGGLES

FIELD OF THE INVENTION

The present invention relates to goggles and more particularly to a safety goggles with improved characteristics.

BACKGROUND OF THE INVENTION

As is known that a goggles is designed to protect the eyes against dust, sparks, etc. by fitted side guides. But this is unsatisfactory for the purpose for which the invention is concerned for being monotonous both in functionality and design. For example, a coupled shade pivotal with respect to goggles has not been proposed in any disclosure. As such, improvement exists.

SUMMARY OF THE INVENTION

It is thus an object of the present invention to provide a safety goggles comprising a frame including an attachment member projected above the top center, a slanted coupling surface on the top of the attachment member, and a flange; a lens fitted in the frame; a protector guide including an annular groove on the front edge with the flange of the frame fitted in; a shade including a frame, an opening defined by the frame, a flange extended inward from the frame, a plurality of studs on the frame of the shade, a plurality of projections on either inner side of the flange of the shade, an engagement member projected above the top center of the flange of the shade, and an inclined coupling surface on the top of the engagement member; a protector lens including a plurality of holes on the periphery being snugly engaged with the studs when the protector lens is fitted into the shade; a dark lens abutted on the protector lens; and an abutment member including a plurality of alternate risers on the front peripheral edge, the abutment member being abutted on the dark lens within the shade such that the projections is capable of securing the abutment member to the dark lens, wherein the shade is pivotable at an angle of either 90 degrees or 180 degrees with respect to the frame when the engagement member is engaged with the attachment member with the inclined coupling surface slidingly engaged with the slanted coupling surface.

The above and other objects, features and advantages of the present invention will become apparent from the following detailed description taken with the accompanying drawings.

BRIEF DESCRIPTION OF THE DRAWINGS

FIG. 1 is an exploded view of a safety goggles according to the invention;

FIG. 2 is a cross-sectional view showing the engagement of frame, lens, and guide shown in FIG. 1;

FIG. 3 is a partial exploded view of shade and protector lens shown in FIG. 1;

FIG. 4 is a cross-sectional view showing the engagement of shade and protector lens shown in FIG. 3;

FIG. 5 is a view similar to FIG. 3 showing shade and abutment member shown in FIG. 1;

DETAILED DESCRIPTION OF THE PREFERRED EMBODIMENTS

Figure 7:
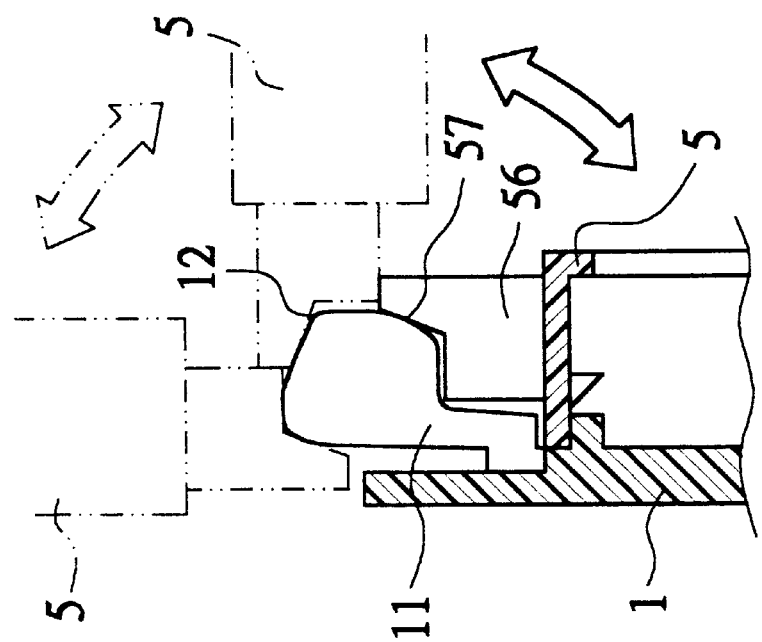
FIG. 7 is a cross-sectional view schematically showing the angle adjustment operation of shade with respect to frame shown in FIG. 1.
Figure 6:
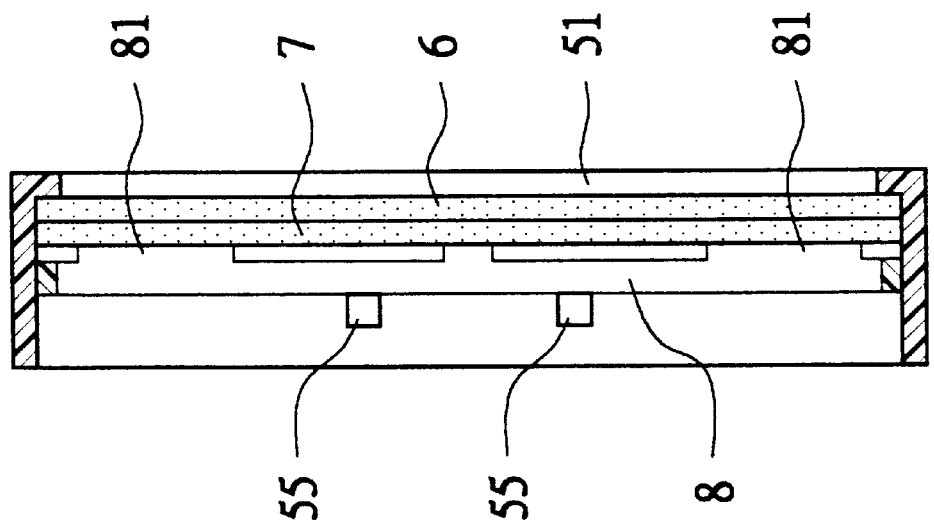
FIG. 6 is a cross-sectional view showing the engagement of shade, protector lens, dark lens, and abutment member shown in FIG. 1.
Figure 8:
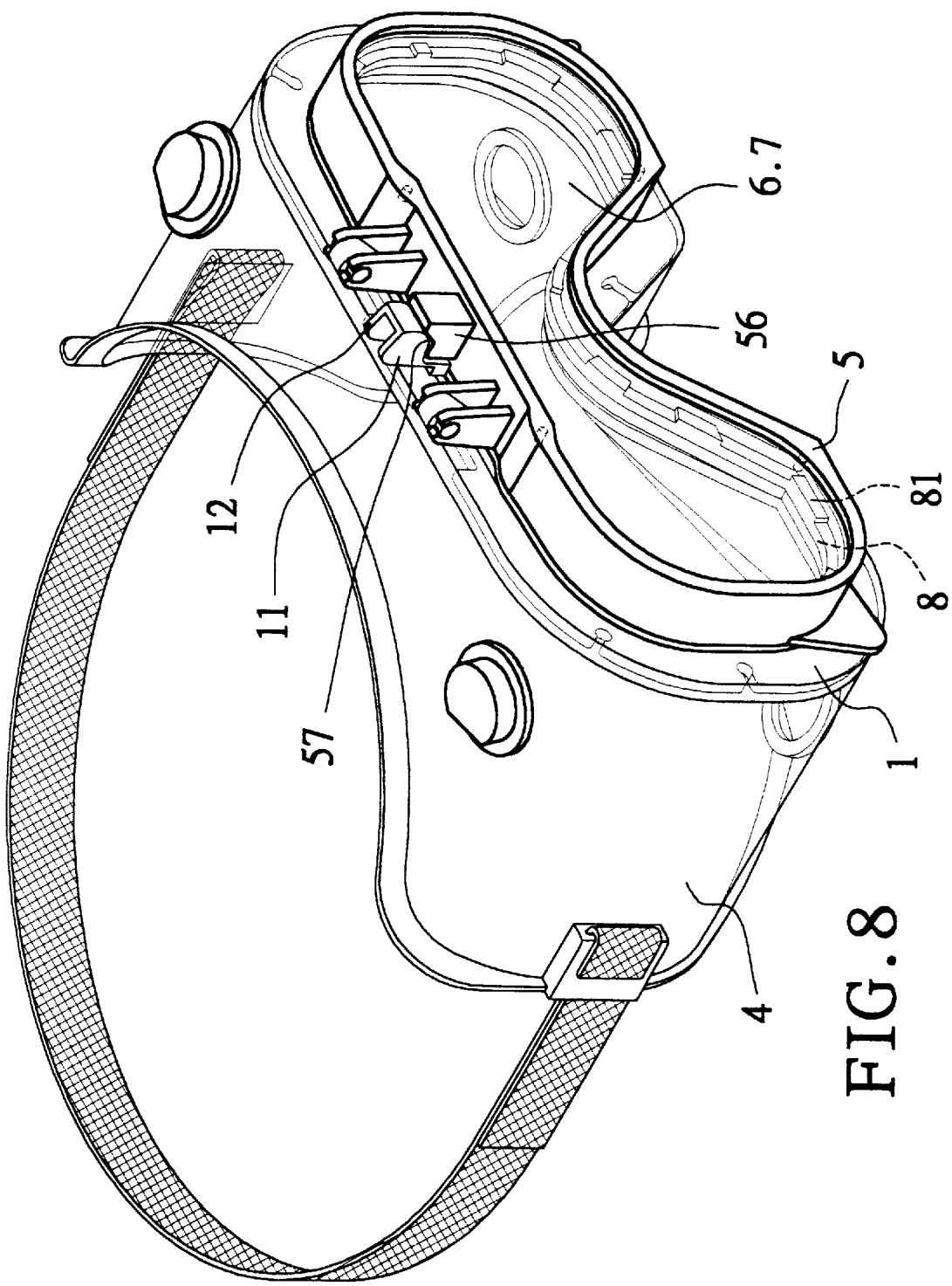
FIG. 8 is a perspective view of the assembled goggles shown in FIG. 1.
Figure 9:
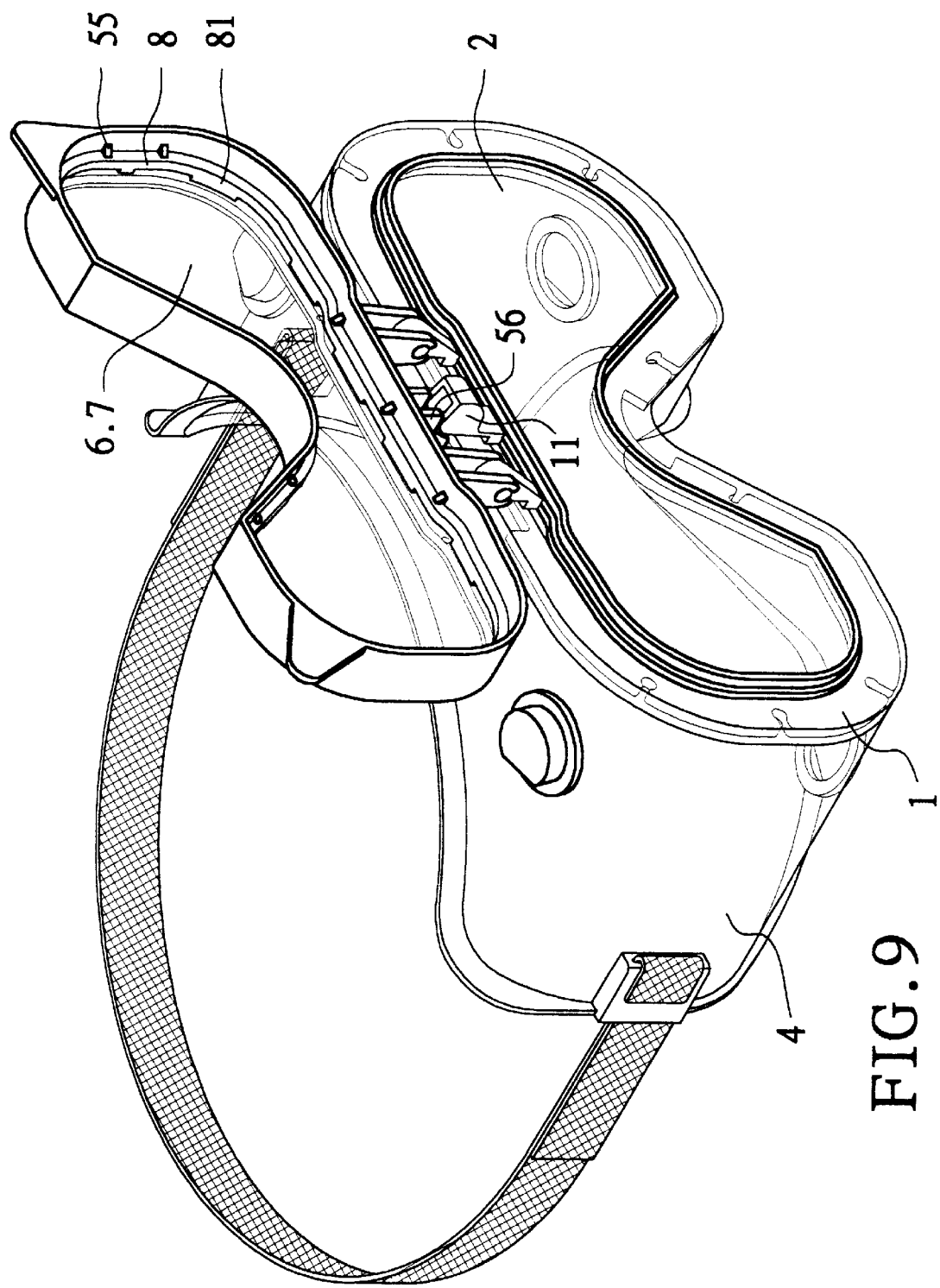
FIG. 9 is a view similar to FIG. 8, but showing shade pivoted 180 degrees with respect to frame shown in FIG. 1.

Referring to the accompanying drawings and particularly to FIG. 1, there is shown a safety goggles constructed in accordance with the invention comprising a frame 1, a lens 2 fitted in frame 1, a guide 4 fitted with frame 1 for protecting the eyes against foreign objects, a shade 5 pivotable with respect to frame 1 by a mechanism as detailed later, a protector lens 6, a dark lens 7, and an abutment member 8 wherein protector lens 6, dark lens 7, and abutment member 8 are mounted in the frame of shade 5 as detailed later. As shown in FIGS. 3 and 4, a plurality of studs 53 are provided on the frame 52 of shade 5. Also, a plurality of holes 61 are provided on the periphery of protector lens 6 being snugly engaged with studs 53 when protector lens 6 is fitted into the opening 51 defined by the frame 52 of shade 5. As shown in FIG. 5, two projections 55 are provided on either inner side of the flange 54 of shade 5. A dark lens 7 is abutted on protector lens 6 as shown in FIG. 6. Also, abutment member 8 is a frame structure and has a plurality of alternate risers 81 formed on the front edge as shown in FIG. 5. Abutment member 8 is abutted on dark lens 7 within shade 8 as shown in FIG. 6 wherein projections 55 are served to secure abutment member 8 to dark lens 7. As shown in FIGS. 7 to 9, an engagement member 56 is projected above the top center of the flange 54 of shade 5. An inclined coupling surface 57 is formed on the top of engagement member 56. An attachment member 11 is projected above the top center of the frame 1. A slanted coupling surface 12 is formed on the top of attachment member 11. Engagement member 56 and attachment member 11 are shown in the assembled state of goggles in FIG. 8 with the inclined coupling surface 57 slidingly engaged with the slanted coupling surface 12. Further, shade 5 is permitted to pivot at an angle of 90 degrees (indicated by dashed lines in FIG. 7) or 180 degrees (see FIGS. 7 and 9) with respect to frame 1 when engagement member 56 is engaged with attachment member 11. As shown in FIG. 2, an annular groove 41 is provided on the front edge of guide 4 with the flange 13 of frame 1 fitted in wherein as stated above, lens 2 has been fitted in frame 1.

While the invention has been described by means of specific embodiments, numerous modifications and variations could be made thereto by those skilled in the art without departing from the scope and spirit of the invention set forth in the claims.

What is claimed is:

1. A safety goggles comprising:

a frame including an attachment member projected above a top center, a slanted coupling surface on the top of the attachment member, and a flange;

a lens fitted in the frame;

a protector guide including an annular groove on the front edge with the flange of the frame fitted in;

a shade including a frame, an opening defined by the frame, a flange extended inward from the frame, a plurality of studs on the frame of the shade, a plurality of projections on either inner side of the flange of the shade, an engagement member projected above the top center of the flange of the shade, and an inclined coupling surface on the top of the engagement member;

a protector lens including a plurality of holes on the periphery being snugly engaged with the studs when the protector lens is fitted into the shade;

a dark lens abutted on the protector lens; and an abutment member including a plurality of alternate risers on the front peripheral edge, the abutment member being abutted on the dark lens within the shade such that the projections are capable of securing the abutment member to the dark lens, wherein the shade is pivotable at an angle of either 90 degrees or 180 degrees with respect to the frame when the engagement member is engaged with the attachment member with the inclined coupling surface slidingly engaged with the slanted coupling surface.

* * * * *